United States Patent [19]

Lombardino

[11] Patent Number: 4,610,982

[45] Date of Patent: Sep. 9, 1986

[54] ANTI-INFLAMMATORY BENZO- AND THIENO-1,2-THIAZINE-3-CARBOXAMIDE 1,1-DIOXIDE DERIVATIVES, COMPOSITIONS, AND METHOD OF USE THEREFOR

[75] Inventor: Joseph G. Lombardino, Niantic, Conn.

[73] Assignee: Pfizer Inc., New York, N.Y.

[21] Appl. No.: 740,466

[22] Filed: Jun. 3, 1985

[51] Int. Cl.[4] .................. A61K 31/38; C07D 279/02; C07D 513/04

[52] U.S. Cl. ...................................... 514/225; 544/48; 544/49

[58] Field of Search ...................... 544/48, 49; 514/225

[56] References Cited

U.S. PATENT DOCUMENTS

| | | | |
|---|---|---|---|
| 3,591,584 | 7/1971 | Lombardino | 260/243 |
| 3,646,020 | 2/1972 | Zinnes et al. | 544/49 |
| 3,704,298 | 11/1972 | Zinnes et al. | 544/49 |
| 3,788,324 | 1/1974 | Zinnes et al. | 260/243 |
| 3,822,258 | 7/1974 | Zinnes et al. | 260/243 R |
| 4,180,662 | 12/1979 | Pfister et al. | 544/48 |
| 4,224,445 | 9/1980 | Hromatka et al. | 544/48 |
| 4,309,427 | 1/1981 | Lombardino | 424/246 |
| 4,376,768 | 3/1983 | Ozaki et al. | 424/246 |
| 4,434,164 | 2/1984 | Lombardino | 424/246 |
| 4,540,692 | 9/1985 | Ueda et al. | 544/49 |

OTHER PUBLICATIONS

J. G. Lombardino et al., "Potent Antiinflammatory N-Heterocyclic 3-Carboxamides of 4-Hydroxy-2-methyl-2H-1,2-benzothiazine 1,1-Dioxide", *Journal of Medicinal Chemistry*, vol. 16, No. 5, p. 493 (1973).

*Primary Examiner*—Henry R. Jiles
*Assistant Examiner*—J. G. Mullins
*Attorney, Agent, or Firm*—Charles J. Knuth; Peter C. Richardson

[57] ABSTRACT

Certain novel 2-acetoxybenzoyl and ring-substituted α-arylpropionyl derivatives of 4-hydroxy-2-methyl-N-(2-pyridinyl)-2H-1,2-benzothiazine-3-carboxamide 1,1-dioxide and several other closely-related known oxicams have been prepared. These particular compounds are useful in therapy as non-steroidal anti-arthritic agents. Typical member compounds include 4-(2-acetoxybenzoyloxy)-2-methyl-N-(2-pyridinyl)-2H-1,2-benzothiazine-3-carboxamide 1,1-dioxide, 4-[α-(4-isobutylphenyl)propionyloxy]-2-methyl-N-(2-pyridinyl)-2H-1,2-benzothiazine-3-carboxyamide N-(2-pyridinyl)-2H-1,2-benzothiazine-3-carboxyamide 1,1-dioxide, 4-[α-(3-benzoylphenyl)propionyloxy]-2-methyl-N-(2-pyridinyl)-2H-1,2-benzothiazine-3-carboxamide 1,1-dioxide, "d-4-[α-6-methoxynaphth-2-yl)propionyloxy]-2-methyl-N-(2-pyridinyl)-2H-1,2-benzothiazine-3-carboxamide 1,1-dioxide" to -- d-4-[α-(6-methoxynaphth-2-yl)propionyloxy]-2-methyl-N-(2-pyridinyl)-2H-1,2-benzothiazine-3-carboxamide 1,1-dioxide.

14 Claims, No Drawings

ANTI-INFLAMMATORY BENZO- AND THIENO-1,2-THIAZINE-3-CARBOXAMIDE 1,1-DIOXIDE DERIVATIVES, COMPOSITIONS, AND METHOD OF USE THEREFOR

BACKGROUND OF THE INVENTION

This invention relates to new and useful benzothiazine dioxide derivatives. More particularly, it is concerned with certain novel 2-acetoxybenzoyl and ring-substituted α-arylpropionyl derivatives of 4-hydroxy-2-methyl-N-(2-pyridinyl)-2H-1,2-benzothiazine-3-carboxamide 1,1-dioxide and several other closely-related oxicams, which are of especial value in view of their unique chemotherapeutic properties.

In the past, various attempts have been made to obtain new and better anti-inflammatory agents. For the most part, these efforts have involved the synthesis and testing of various steroidal compounds such as the corticosteroids or non-steroidal substances of an acidic nature such as phenylbutazone, indomethacin and the like, including a new agent known as piroxicam. The latter substance is a member of a class of anti-inflammatory/analgesic N-heteroaryl-4-hydroxy-2-methyl-2H-1,2-benzothiazine-3-carboxamide 1,1-dioxides (known as oxicams) described and claimed in U.S. Pat. No. 3,591,584 and is specifically, 4-hydroxy-2-methyl-N-(2-pyridinyl)-2H-1,2-benzothiazine-3-carboxamide 1,1dioxide. Other agents of this type are disclosed in U.S. Pat. Nos. 3,787,324, 3,822,258, 4,180,662 and 4,376,768. In U.S. Pat. No. 4,434,164, there are specifically described and claimed the ethylenediamine, monoethanolamine and diethanolamine salts of 4-hydroxy-2-methyl-N-(2-pyridinyl)-2H-1,2-benzothiazine-3-carboxamide 1,1-dioxide, which are particularly valuable in pharmaceutical dosage forms as non-steroidal therapeutic agents for the treatment of painful inflammatory conditions, such as those caused by rheumatoid arthritis, since they are all crystalline, non-hygroscopic, rapidly-dissolving solids with high water solubility. In U.S. Pat. No. 4,309,427, there are disclosed certain novel acyl derivatives of 4-hydroxy-2-methyl-N-(2-pyridinyl)-2H-1,2-benzothiazine-3-carboxamine 1,1-dioxide and 4-hydroxy-2-methyl-N-(6-methyl-2-pyridinyl)-2H-1,2-benzothiazine-3-carboxamide 1,1-dioxide, which are useful as non-steroidal therapeutic agents for alleviating various inflammatory conditions, including those of the skin, especially when given by the topical route of administration. However, in the continuing search for still more improved anti-inflammatory/analgesic agents, there is a need for anti-arthritic agents that are orally administrable and yet at the same time are less ulcerogenic than the parent oxicam compounds of the prior art.

SUMMARY OF THE INVENTION

In accordance with the present invention, it has now been found that certain novel 2-acetoxybenzoyl and ring-substituted α-arylpropionyl derivatives of 4-hydroxy-2-methyl-N-(2-pyridinyl)-2H-1,2-benzothiazine-3-carboxamide 1,1-dioxide and several other closely-related known oxicams are useful in therapy as nonsteroidal therapeutic agents for alleviating painful inflammatory conditions such as those caused by rheumatoid arthritis, for example. The novel compounds of this invention are of the formula.

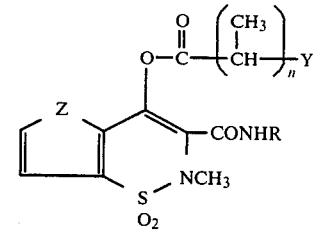

wherein R is 2-pyridyl, 6-methyl-2-pyridyl, 6-fluoro-2-pyridyl, 6-chloro-2-pyridyl, 5-methyl-3-isoxazolyl or 2-thiazolyl; Y is 4-isobutylphenyl, 3-phenoxyphenyl, 3-benzoylphenyl, 2-acetoxyphenyl, 6-methoxynaphth-2-yl or 2-fluoro-4-biphenylyl; Z is —CH=CH— or S; and n is zero or one, with the proviso that n is one when Y is other than 2-acetoxyphenyl and n is zero when Y is 2-acetoxyphenyl.

The compounds of this invention are useful in therapy, as aforesaid, as valuable non-steroidal therapeutic agents for the treatment of painful inflammatory conditions, especially those caused by rheumatoid arthritis, and are particularly adapted for use in various pharmaceutical dosage forms, including those designed for oral, topical and parenteral administration. Moreover, the anti-inflammatory compounds of this invention are unusual in that they lack cyclooxygenase inhibitory activity and are less ulcerogenic than the parent acidic oxicams from which they are derived. Additionally, hydrolysis of these novel products in vivo simultaneously produces in each and every instance two different anti-inflammatory compounds of known value. Accordingly, the preferred method of administration for the presently-claimed compounds is oral, particularly in view of the aforementioned advantageous properties which they possess.

Of especial interest in this connection are such typical and preferred member compounds of the invention as 4-(2-acetoxybenzoyloxy)-2-methyl-N-(2-pyridinyl)-2H-1,2-benzothiazine-3-carboxamide 1,1-dioxide, 4-[α-(4-isobutylphenyl)propionyloxy]-2-methyl-N-(2-pyridinyl)-2H-1,2-benzothiazine-3-carboxamide 1,1-dioxide, 4-[α-(3-benzoylphenyl)propionyloxy]-2-methyl-N-(2-pyridinyl)-2H-1,2-benzothiazine-3-carboxamide 1,1-dioxide,'d-4-[α-6-methoxynaphth-2-yl)propionyloxy]-2-methyl-N-)(2-pyridinyl)-2H-1,2-benzothiazine-3-carboxamide 1,1-dioxide" to d-4-[α-(6-methoxynaphth-2-yl)propionyloxy]-2-methyl-N-(2-pyridinyl)-2H-1,2-benzothiazine-3-carboxamide 1,1-dioxide respectively. These particular compounds are especially effective in treating many painful inflammatory conditions by the oral route of administration.

DETAILED DESCRIPTION OF THE INVENTION

In the process for preparing the novel compounds of this invention, the parent oxicam compound of the formula:

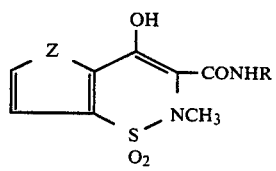

wherein R and Z are each defined as aforesaid, is treated with at least an equivalent amount in moles of an acyl halide of the formula:

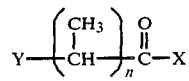

wherein Y and n are each previously defined and X is either chlorine or bromine. This reaction is normally carried out in a reaction-inert organic solvent under substantially anhydrous conditions in the presence of at least an equivalent amount of an appropriate standard base. In general, the reaction is conducted at a temperature of from about 0° C. up to about 50° C. for a period of about one-half to about 72 hours, although it is usually most convenient to carry out the reaction at or about room temperature after combining the reactants together at a reduced temperature, e.g. 0 to 10° C. Although any inert organic solvent may be used, it is generally most desirable to employ such solvents as aromatic hydrocarbons, halogenated lower hydrocarbons, lower alkyl ketones, lower alkyl esters of lower alkane hydrocarbon carboxylic acids, lower dialkyl ethers, dioxane and tetrahydrofuran. Preferred aromatic hydrocarbons include benzene, toluene and xylene; preferred halogenated lower hydrocarbons include methylene chloride, chloroform, ethylene dichloride and s-tetrachlorethane; preferred lower alkyl ketones include acetone, methyl ethyl ketone and methyl isobutyl ketone; preferred lower alkyl esters include methyl acetate, ethyl acetate, isopropyl acetate, methyl propionate and ethyl propionate; while preferred lower dialkyl ethers include diethyl ether, diisopropyl ether and di-n-butyl ether. Appropriate standard bases for use in this process include the alkali metal and alkaline-earth metal oxides, bicarbonates and carbonates, such as magnesium oxide, sodium bicarbonate, sodium carbonate and magnesium carbonate, as well as tertiary amines such as triethylamine and pyridine. It should be noted that the standard base employed must be present in sufficient amount to neutralize the liberated hydrogen halide formed in the reaction. Triethylamine is most preferred because it can easily be removed from the reaction mixture in the form of an insoluble solid hydrohalide precipitate.

The reaction is conveniently followed by thin-layer chromatography, thereby determining reaction times sufficient to provide complete reaction and at the same time avoiding unnecessary heating costs and excessive reaction time, which can increase the level of by-products and reduce yields.

The starting materials required for preparing the novel 2-acetoxybenzoyl and ring-substituted α-arylpropionyl derivatives of this invention are all known compounds. For instance, 4-hydroxy-2-methyl-N-(2-pyridinyl)-2H-1,2-benzothiazine-3-carboxamide 1,1dioxide, 4-hydroxy-2-methyl-N-(6-methyl-2-pyridinyl)-2H-1,2-benzothiazine-3-carboxamide 1,1-dioxide and 4-hydroxy-2-methyl-N-(2-thiazolyl)-2H-1,2-benzothiazine-3-carboxamide 1,1-dioxide are all fully described in U.S. Pat. No. 3,591,584 to J. G. Lombardino, as well as in the paper to J. G. Lombardino et al., appearing in the *Journal of Medicinal Chemistry*, Vol. 16, p. 493 (1973), including their synthesis from readily available organic materials. The other closely-related oxicams required as starting materials in the process of this invention are readily available by methods well known to those skilled in the art, e.g., see the patent references to the other oxicams cited in the background section of the instant specification.

The acyl halide compounds employed as acylating agents in the herein described process of this invention, on the other hand, are essentially new compounds, which are prepared by treating the corresponding organic acids with an appropriate halogenating agent like thionyl chloride or bromide, or oxalyl chloride, in accordance with the conventional methods of organic synthesis as hereinafter described in the experimental section of this specification. (see Preparations A-F). The organic acid starting materials from which the acyl halides are derived are all known drugs and are identified in Preparations A-F.

The novel 2-acetoxybenzoyl and ring-substituted α-arylpropionyl oxicam esters of the present invention are all readily adapted to therapeutic use as antiarthritic agents. For instance, 4-[α-(3-benzoylphenyl)-propionyloxy]-2-methyl-N-(2-pyridinyl)-2H-1,2-benzothiazine-3-carboxamide 1,1-dioxide, a typical and preferred agent of the present invention, exhibits anti-inflammatory activity in the standard carrageenininduced rat foot edema test [described by C. A. Winter et al., *Proc. Soc. Exp. Biol. Med.*, Vol. 111, p. 544 (1962)], where it was found to cause a 64% inhibition in swelling at the 32 mg./kg. dose level when given by the oral route. The herein described 2-acetoxybenzoyl and ring-substituted α-arylpropionyl derivatives exhibit additional advantages. For instance, 4-[α-(3-benzoylphenyl)propionyloxy]-2-methyl-N-(2-pyridinyl)-2H-1,2-benzothiazine-3-carboxamide 1,1-dioxide has an $IC_{50}$ value of 0.02/10 μM with respect to lipoxygenase/cyclooxygenase inhibition, thereby indicating that it lacks cyclooxygenase inhibitory activity to a substantial degree and is therefore considerably less ulcerogenic than the oxicam from which it is derived. Additionally, hydrolysis of this novel product in vivo simultaneously produces two different anti-inflammatory compounds of known value (viz., piroxicam and ketoprofen). The other oxicam ester compounds of this invention also afford similar results.

The herein described oxicam esters of this invention can be administered via either the oral, parenteral or topical routes. In general, these compounds are most desirably administered in doses ranging from about 5.0 mg. up to about 1000 mg. per day, although variations will necessarily occur depending upon the weight and condition of the subject being treated and the particular route of administration chosen. However, a dosage level that is in the range of from about 0.08 mg. to about 16 mg. per kg. of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing harmful side effects provided that such higher dose levels are first divided into several small doses for administration throughout the day.

The oxicam esters of this invention may be administered alone or in combination with pharmaceutically acceptable carriers by either of the three routes previously indicated. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 0.5% to about 90% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium sterarate, sodium lauryl sulfate and talc are often very useful for tabletting purposes. Solid compositions of a similar type may also be employed as fillers in gelatin capsules; preferred materials also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of these oxicam esters in either sesame or peanut oil or in aqueous propylene glycol may be employed. The aqueous solutions should be suitably buffered (pH 8) if necessary and the liquid diluent first rendered isotonic. These aqueous solutions are suitable for intravenous injection purposes. The oily solutions are suitable for intra-articular, intramuscular and subcutaneous injection purposes. Additionally, it is also possible to administer the aforesaid oxicam esters topically when treating inflammatory conditions of the skin or eye and this may be preferably done by way of creams, jellies, pastes, ointments, solutions and the like, in accordance with standard pharmaceutical practice.

The anti-inflammatory activity of the compounds of the present invention is demonstrated in the previously mentioned standard carrageenin-induced rat foot edema test. In this test, anti-inflammatory activity is determined as the percent inhibition of edema formation in the hind paw of male albino rats (weighing 150–190g.) in response to a sub-plantar injection of carrageenin. The carrageenin is injected as a 1% aqueous suspension (0.015 ml.) one hour after oral administration of the drug, which is normally given in the form of an aqueous solution. Edema formation is then assessed by measuring the volume of the injected paw initially as well as three hours after the carrageenin injection. The increase in volume three hours after carrageenin injection constitutes the individual response. Compounds are considered active if the difference in response between the drug-treated animals (six rats/group) and a control group receiving the vehicle alone is significant on comparison with the results afforded by a standard compound like phenylbutazone at 33 mg./kg., via the oral route of administration.

PREPARATION A

To a well-stirred suspension consisting of 10.0 g. (0.0555 mole) of acetylsalicylic acid (aspirin) in 100 ml. of methylene chloride, there were added in a dropwise manner 14.1 g. (0.111 mole) of oxalyl chloride (9.68 ml.) dissolved in 20 ml. of methylene chloride. The resulting reaction mixture was then refluxed for a period of two hours and finally cooled to room temperature ($\sim 20°$ C.). The clear colorless solution so obtained was concentrated in vacuo to dryness to yield a residue that was substantially free of solvent and excess oxalyl chloride. In this way, there were readily obtained 11.7 g. of substantially pure 2-acetoxybenzoyl chloride (acetylsalicylyl chloride) in the form of a clear colorless liquid. The latter product (which was characterized by means of infrared absorption spectra) was used as such in the next reaction step without any purification being necessary. The yield of product was assumed to be quantitative.

PREPARATION B

To a well-stirred solution consisting of 3.1 g. (0.015 mole) of $\alpha$-(4-isobutylphenyl)propionic acid (ibuprofen) dissolved in 200 ml. of methylene chloride, there were added 3.8 g. (0.030 mole) of oxalyl chloride. The resulting reaction mixture was refluxed for a period of two hours and then cooled to room temperature. The clear colorless solution so obtained was thereafter concentrated in vacuo to dryness to yield a residue that was substantially free of solvent and excess oxalyl chloride. In this way, there was readily obtained substantially pure $\alpha$-(4-isobutylphenyl)-propionyl chloride in the form of a clear colorless oil. The latter product was used as such in the next reaction step without any purification being necessary. The yield of product was assumed to be quantitative.

PREPARATION C

To 500 mg. (0.002 mole) of $\alpha$-(3-benzoylphenyl)-propionic acid (ketoprofen), there were added 8.21 g. (0.069 mole) of thionyl chloride (5 ml.) to form a clear yellow solution. The latter mixture was then heated under reflux for a period of one hour and finally cooled to room temperature. The clear green solution so obtained was concentrated in vacuo to near dryness to remove excess thionyl chloride and the resulting residue thereafter azeotroped with benzene and evaporated to give a yellow oil. In this way, there was obtained substantially pure $\alpha$-(3-benzoylphenyl)propionyl chloride, which was used in the next reaction step without any further purification being necessary. The yield of product was assumed to be quantitative.

PREPARATION D

To 3.0 g. (0.0130 mole) of d- $\alpha$-(6-methoxynaphth-2-yl)propionic acid (naproxen), there were added 10 ml. of thionyl chloride to form an initial mixture that was subsequently refluxed for a period of one hour. At this point, the reaction mixture became a brown solution and was cooled to room temperature. The latter solution was then concentrated in vacuo to dryness, and the resulting residue azeotroped twice with benzene and evaporated to give a crude brown product. Trituration of the latter material with diethyl ether, followed by suction filtration and drying in vacuo to constant weight then gave 1.2 g. (37%) of pure d-α-(6-methoxynaphth-2-yl)propionyl chloride in the form of a crystalline brown solid. The latter product was used as such in the next reaction step without any further purification being necessary.

PREPARATION E

To 500 mg. (0.00189 mole) of α-(3-phenoxyphenyl)propionic acid (fenoprofen), there were cautiously added 7.23 g. (0.057 mole) of oxalyl chloride (5 ml.) to form an almost clear mixture. The latter mixture (after the initial vigorous reaction had subsided) was then heated under reflux for a period of one hour to form a suspension, followed by the addition of 5 ml. of thionyl chloride to the resulting cooled suspension. The new reaction mixture thus obtained was then heated under reflux for a period of one hour to give a grey solution and finally cooled to room temperature. The latter solution was concentrated in vacuo to dryness to remove excess reagent, and the resulting residue was subsequently azeotroped with benzene to ultimately afford substantially pure α-(3-phenoxyphenyl)propionyl chloride. The latter product was used as such in the next reaction step without any further purification being necessary. The yield of product was assumed to be quantitative.

PREPARATION F

To 500 mg.(0.00205 mole) of α-(2-fluoro-4-biphenylyl)propionic acid (flurbiprofen), there were added 8.21 g. (0.069 mole) of thionyl chloride (5 ml.) to form a clear yellow solution. The latter mixture was then heated under reflux for a period of one hour and finally cooled to room temperature. The clear yellow solution so obtained was thereafter concentrated in vacuo to dryness to remove excess thionyl chloride, and the resulting residue was subsequently azeotroped with benzene to give the desired product. In this way, there was readily obtained substantially pure α-(2-fluoro-4-biphenylyl)propionyl chloride, which was used as such in the next reaction step without any further purification being necessary. The yield of product was assumed to be quantitative.

EXAMPLE 1

To a well-stirred solution consisting of 6.5 g. (0.019 mole) of 4-hydroxy-2-methyl-N-(2-pyridinyl)-2H-1,2-benzothiazine-3-carboxamide 1,1-dioxide (prepared as described in U.S. Pat. No. 3,591,584) dissolved in 200 ml. of methylene chloride containing 2.82 g. (0.028 mole) of triethylamine (3.87 ml.) under a dry nitrogen atmosphere, there was added in a dropwise manner a solution consisting of 5.76 g. (0.029 mole) of 2-acetoxybenzoyl chloride (the product of Preparation A) dissolved in 20 ml. of methylene chloride. The resulting mixture was stirred at room temperature (~20° C.) for a period of 18 hours. At this point, the reaction mixture was successively extracted three times with saturated aqueous sodium bicarbonate solution and one time with saturated aqueous sodium chloride. The organic layer was then dried over anhydrous magnesium sulfate, filtered and evaporated to give a red brown foam. The latter material was then placed on a silica gel column and eluted with methylene chloride/ethyl acetate (4:1 by volume) to effect the desired separation. Upon evaporation of the desired eluate, there was obtained crude product material which was thereafter triturated with diethyl ether/ethyl acetate (9:1 by volume) to eventually yield a white solid product. The latter solid was filtered and recrystallized twice from ethyl acetate to finally afford 442 mg. (4%) of pure 4-(2-acetoxybenzoyloxy)-2-methyl-N-(2-pyridinyl)-2H-1,2-benzothiazine-3-carboxamide 1,1-dioxide, m.p. 170°–173° C. The pure product was further characterized by means of thin layer chromatography and infrared absorption spectra, in addition to elemental analysis.

Anal. Calcd. for $C_{24}H_{19}N_3O_7S$: C, 58.41; H, 3.88; N, 8.52. Found: C, 58.20; H, 4.13; N, 8.41.

EXAMPLE 2

To a well stirred solution consisting of 3.8 g. (0.0115 mole) of 4-hydroxy-2-methyl-N-(2-pyridinyl)-2H-1,2-benzothiazine-3-carboxamide 1,1-dioxide dissolved in 200 ml. of methylene chloride containing 1.52 g. (0.015 mole) of triethylamine (209 ml.) under a dry nitrogen atmosphere, there was added in a dropwise manner a solution consisting of 3.37 g. (0.015 mole) of α-(4-isobutylphenyl)propionyl chloride (the product of Preperation B) dissolved in 25 ml. of methylene chloride. The resulting reaction mixture was stirred at room temperature for a period of 18 hours. At this point, the reaction mixture was successively extracted two times with saturated aqueous sodium bicarbonate solution and one time with saturated aqueous sodium chloride. The organic layer was then dried over anhydrous sodium sulfate, filtered and the resulting filtrate was subsequently concentrated in vacuo to give a yellow foam. Recrystallization of the latter material from ethyl acetate/hexane gave 3.6 g. (60%) of pure 4-[α-(4-isobutylphenyl)propionyloxy]-2-methyl-N-(2-pyridinyl)-2H-1,2-benzothiazine-3-carboxamide 1,1-dioxide in the form of white crystals melting at 235°–237° C. The pure product was further characterized by means of thin layer chromatography and infrared absorption spectra, in addition to elemental analysis.

Anal. Calcd. for $C_{28}H_{29}N_3O_5S$: C, 64.72; H, 5.63; N, 8.09. Found: C 64.37; H, 5.75; N, 8.07.

EXAMPLE 3

To a well-stirred solution consisting of 460 mg. (0.00139 mole) of 4-hydroxy-2-methyl-N-(2-pyridinyl)-2H-1,2-benzothiazine-3-carboxamide 1,1-dioxide (piroxicam) dissolved in 35 ml. of methylene chloride containing 197 mg. (0.00195 mole) of triethylamine (0.27 ml.) under a dry nitrogen atmosphere, there was added in a dropwise manner a solution consisting of 545 mg. (0.002 mole) of α-(3-benzoylphenyl)propionyl chloride (the product of Preparation C) dissolved in 15 ml. of methylene chloride. The resulting reaction mixture was stirred at room temperature for a period of four hours. At this point, the reaction mixture was successively extracted two times with saturated aqueous sodium bicarbonate solution and one time with saturated aqueous sodium chloride. The organic layer was then dried over anhydrous sodium sulfate, filtered and the resulting filtrate was subsequently concentrated in vacuo to give a yellow-tan oily residue. Trituration of the latter material with ethyl acetate, followed by filtration and drying gave 128 mg. of yellow solids which proved to be unreacted piroxicam starting material according to thin layer chromatography analysis. The ethyl acetate filtrate obtained from the above step was then concentrated in vacuo to yield a residual material. The latter material was then placed on a column of silica gel and eluted with methylene chloride/ethyl acetate (9:1 by volume) to effect the desired separation. Upon evaporation of the desired eluate, there was obtained crude product in the form of a residual oil that was later dissolved in 25 ml. of methylene chloride. The latter organic solution was subsequently washed with 10 ml. of 3N aqueous sodium hydroxide, and the saved organic layer was thereafter dried over anhydrous magnesium sulfate and filtered. Concentration of the resulting filtrate under reduced pressure then gave 220 mg. (26%) of pure 4-[α-(3-benzoylphenyl)propionyloxy]-2-methyl-N-(2-pyridinyl)-2H-1,2-benzothiazine-3-carboxamide 1,1-dioxide as a yellow foam. The pure product was characterized by means of mass spectroscopy, thin layer chromatography and infrared absorption spectra.

EXAMPLE 4

To a well-stirred solution consisting of 1.14 g. (0.00345 mole) of 4-hydroxy-2-methyl-N-(2-pyridinyl-2H-1,2-benzothiazine-3-carboxamide 1,1-dioxide dissolved in 75 ml. of methylene chloride containing 484 mg. (0.0048 mole) of triethylamine (0.67 ml.) under a dry nitrogen atmosphere, there was added in a dropwise manner a solution consisting of 1.2 g. (0.0048 mole) of d-α-(6-methoxynaphth-2-yl)propionyl chloride (the product of Preparation D) dissolved in 25 ml. of methylene chloride. The resulting reaction mixture was stirred at room temperature for 18 hours. The reaction mixture was then successively extracted two times with saturated aqueous sodium bicarbonate solution and one time with saturated aqueous sodium chloride. The organic layer was then dried over anhydrous sodium sulfate, filtered and concentrated in vacuo to give a yellow foam (yield, 41.8 g.). The latter material was then placed on a column of silica gel and eluted with methylene chloride/ethyl acetate (9:1 by volume) to effect the desired separation. Upon evaporation of the desired eluate, there was obtained 1.0 g. of crude product in the form of a yellow foam that was later stirred into a small amount of toluene. Petroleum ether was then added to the latter mixture with stirring until a gum formed, at which point the solvents were removed by means of decantation. Trituration of the gum with fresh petroleum ether was then effected by stirring the gum with the solvent for a period of one hour, followed by decantation and thereafter repeating the entire process two more times. Finally, the gum was allowed to stir with fresh petroleum ether for approximately 64 hours and this eventually caused the formation of a fine white powder. This powder was collected by means of suction filtration, washed well with diethyl ether and thereafter dried in vacuo to constant weight to ultimately afford 620 mg. (33%) of pure d-4-[α-(6-methoxynaphth-2-yl)propionyloxy]-2-methyl-N-(2-pyridinyl) -2H-1,2-benzothiazine-3-carboxamide 1,1-dioxide m.p. 125 C. The pure product was further characterized by means of thin layer chromatography and elemental analysis.

Anal. Calcd. for $C_{29}H_{25}N_3O_2S$ : C, 64.07; H, 4.64; N, 7.73. Found: C, 63.87; H, 4.68; N, 7.74.

EXAMPLE 5

To a well-stirred solution consisting of 450 mg. (0.00135 mole) of 4-hydroxy-2-methyl-N-(2-pyridinyl)-2H-1,2-benzothiazine-3-carboxamide 1,1-dioxide dissolved in 50 ml. of methylene chloride containing 191 mg. (0.00189 mole) of triethylamine (0.26 ml.) under a dry nitrogen atmosphere, there was added in a dropwise manner a solution consisting of 492 mg. (0.00189 mole) of α-(3-phenoxyphenyl)propionyl chloride (the product of Preparation E) dissolved in 25 ml. of methylene chloride. The resulting reaction mixture was stirred at room temperature for four hours. At this point, the reaction mixture was successively extracted two times with saturated aqueous sodium bicarbonate solution and one time with saturated aqueous sodium chloride. The organic layer was then dried over anhydrous sodium sulfate, filtered and concentrated to give a red brown oil. The latter material was then placed on a column of silica gel and eluted with methylene chloride/ethyl acetate (9:1 by volume) to effect the desired separation. Upon evaporation of the desired eluate, there was obtained essentially pure product in the form of a yellow oil that was later placed under a high vacuum for a period of three hours. In this way, there was ultimately obtained 230 mg. (31%) pure 2-methyl-4-α-(3-phenoxyphenyl)propionyloxy]-N-(2-pyridinyl)-2H-1,2-benzothiazine-3-carboxamide 1,1-dioxide hydrate (m.p. 80°–85° C.) in the form of a yellow-white foam. The pure product was further characterized by means of mass spectroscopy, thin layer chromatography and infrared absorption spectra, in addition to elemental analysis.

Anal. Calcd. for $C_{30}H_{25}N_3O_6S.H_2O$: C, 62.81; H, 4.75; N, 7.33. Found: C, 63.09; H, 4.81; N, 6.48.

EXAMPLE 6

To a well-stirred solution consisting of 485 mg. (0.00146 mole) of 4-hydroxy-2-methyl-N-(2-pyridinyl)-2H-1,2-benzothiazine-3-carboxamide 1,1-dioxide dissolved in 35 ml. of methylene chloride containing 207 mg. (0.00205 mole) of triethylamine (0.29 ml.) under a nitrogen atmosphere, there was added in a dropwise manner a solution consisting of 539 mg. (0.00205 mole) of α-(2-fluoro-4-biphenylyl)propionyl chloride (the product of Preparation F) dissolved in 15 ml. of methylene chloride. Upon completion of this step, the resulting reaction was stirred at room temperature for four hours. At this point, the reaction mixture was successively extracted two times with saturated aqueous sodium bicarbonate solution and one time with saturated aqueous sodium chloride. The organic layer was then dried over anhydrous sodium sulfate, filtered and the resulting filtrate was subsequently concentrated in vacuo to an oily yellow residue. Trituration of the latter material with ethyl acetate, followed by suction filtration and drying gave 325 mg. of pale yellow solids which proved to be unreacted piroxicam starting material according to thin layer chromatography analysis. The ethyl acetate filtrate obtained from the above step was then concentrated in vacuo to yield a residual material. The latter material was then placed on a column of silica gel and eluted with methylene chloride/ethyl acetate (9:1 by volume) to effect the desired separation. Upon evaporation of the desired eluate, there was obtained crude product in the form of a residual viscous yellow oil (yield, ca. 300 mg.) that was later dissolved in 10 ml. of methylene chloride. The latter organic solution was subsequently washed with 10 ml. of 3N aqueous sodium hydroxide, and the saved organic layer was thereafter dried over anhydrous sodium sulfate and filtered. Concentration of the resulting filtrate gave 180 mg. (22%) of pure 4-[α-(2-fluoro-4-biphenylyl)propionyloxy]-2-methyl-N-(2-pyridinyl)-2H-1,2-benzothiazine-3-carboxamide 1,1-dioxide as a yellow oil, which slowly crystallized to a yellow solid melting at 110°–115° C. The pure product was further characterized by means of mass spectroscopy, thin layer chromatography and infrared absorption spectra.

I claim:

1. A compound of the formula:

$$\begin{array}{c} \text{O} \quad (CH_3) \\ \parallel \quad | \\ \text{O}-\text{C}-(\text{CH})_n-\text{Y} \\ \text{Z} \diagdown \diagup \\ \| \\ \diagup \diagdown \text{CONHR} \\ \text{S} \diagdown \text{NCH}_3 \\ \text{O}_2 \end{array}$$

wherein

R is 2-pyridyl, 6-methyl-2-pyridyl, 6-fluoro-2-6-chloro-2-pyridyl, 5-methyl-3-isoxazolyl or 2-thiazolyl;

Y is 4-isobutylphenyl, 3-phenoxyphenyl, 3-benzoylphenyl,-2-acetoxyphenyl, 6-methoxynaphth-2-yl or 2-fluoro-4-biphenylyl;

Z is —CH=CH— or S; and n is zero or one, with the proviso that n is one when Y is other than 2-acetoxyphenyl and n is zero when Y is 2-acetoxyphenyl.

2. A compound as claimed in claim 1 wherein Z is S.

3. A compound as claimed in claim 1 wherein Z is —CH=CH—.

4. A compound as claimed in claim 3 wherein R is 2-pyridyl.

5. A compound as claimed in claim 3 wherein R is 6-methyl-2-pyridyl.

6. A compound as claimed in claim 4 wherein n is zero.

7. A compound as claimed in claim 4 wherein n is one.

8. A compound as claimed in claim 7 wherein Y is 4-isobutylphenyl.

9. A compound as claimed in claim 7 wherein Y is 3-phenoxyphenyl.

10. A compound as claimed in claim 7 wherein Y is 3-benzoylphenyl.

11. A compound as claimed in claim 7 wherein Y is 6-methoxynaphth-2-yl.

12. A compound as claimed in claim 7 wherein Y is 2-fluoro-4-biphenylyl.

13. An anti-inflammatory composition comprising a pharmaceutically acceptable carrier and an effective anti-inflammatory amount of a compound as claimed in claim 1.

14. A method for treating inflammatory conditions in a warm-blooded animal, which comprises administering to said animal an effective anti-inflammatory amount of a compound as claimed in claim 1.

* * * * *